US006671548B1

(12) United States Patent
Mouchawar et al.

(10) Patent No.: US 6,671,548 B1
(45) Date of Patent: Dec. 30, 2003

(54) IMPLANTABLE STIMULATION DEVICE AND METHOD FOR DISCRIMINATION ATRIAL AND VENTRICULAR ARRHYTHMIAS

(75) Inventors: Gabriel A. Mouchawar, Newhall, CA (US); Anne M. Street, San Rafael, CA (US); Steven W. Badelt, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 465 days.

(21) Appl. No.: 09/651,287

(22) Filed: Aug. 30, 2000

Related U.S. Application Data

(60) Provisional application No. 60/173,526, filed on Dec. 29, 1999.

(51) Int. Cl.[7] .............................................. A61N 1/362
(52) U.S. Cl. ...................................... 607/14; 600/518
(58) Field of Search ........................... 607/4, 5, 14, 25, 607/9; 600/515, 516, 518

(56) References Cited

U.S. PATENT DOCUMENTS

| | | | |
|---|---|---|---|
| 4,712,555 A | 12/1987 | Thornander et al. | ........ 128/419 |
| 4,774,952 A | 10/1988 | Smits | ......................... 128/419 |
| 4,788,980 A | 12/1988 | Mann et al. | ................ 128/419 |
| 4,796,620 A | 1/1989 | Imran | |
| 4,809,697 A | 3/1989 | Causey, III et al. | ........ 128/419 |
| 4,940,052 A | 7/1990 | Mann et al. | ................ 128/419 |
| 4,944,298 A | 7/1990 | Sholder | ...................... 128/419 |
| 4,944,299 A | 7/1990 | Silvian | ........................ 128/419 |
| 4,969,465 A | 11/1990 | Pless et al. | |
| 4,971,058 A | 11/1990 | Pless et al. | |
| 4,991,603 A | 2/1991 | Cohen et al. | ............... 128/786 |
| 4,998,975 A | 3/1991 | Cohen et al. | ............... 128/419 |
| 5,086,772 A | 2/1992 | Larnard et al. | |
| 5,107,850 A | 4/1992 | Olive | |
| 5,193,535 A | 3/1993 | Bardy et al. | ................ 128/419 |
| 5,257,621 A | 11/1993 | Bardy et al. | |
| 5,327,900 A | 7/1994 | Mason et al. | |
| 5,370,125 A | 12/1994 | Mason et al. | |
| 5,379,776 A | 1/1995 | Murphy et al. | |
| 5,403,352 A | 4/1995 | Rossing | |
| 5,480,413 A | 1/1996 | Greenhut et al. | ............. 607/14 |
| 5,591,215 A | 1/1997 | Greenhut et al. | |
| 5,730,141 A | 3/1998 | Fain et al. | |
| 5,755,736 A * | 5/1998 | Gillberg et al. | ................ 607/4 |
| 5,978,700 A * | 11/1999 | Nigam | ....................... 600/518 |
| 6,272,377 B1 * | 8/2001 | Sweeney et al. | ........... 600/515 |

\* cited by examiner

*Primary Examiner*—George R. Evanisko

(57) ABSTRACT

By redistributing the running totals for various preliminary classifications to other preliminary classifications based upon the values of the most recent cardiac events, the present invention biases the running totals (thereby biasing the duration criteria) to help overcome common discrimination problems which permits the stimulation device to make a correct and final therapy decision more quickly. To identify a patient's heart rhythm, various electrical events such as P-waves and R-waves, and their timing, relationship, and stability, are detected and a preliminary classification is made for each detected event. Running totals of the numbers of all events detected within each of the preliminary classifications are maintained, along with sliding totals covering only the most recently detected events. Then, the arrhythmia is identified based upon an analysis of both the running totals and the sliding totals. In a preferred embodiment, the arrhythmia is identified by first determining whether the sliding total of the number of detected events in any one of the preliminary classifications exceeds a corresponding sliding total threshold. If so, the running totals are then selectively redistributed based upon the sliding totals. The final decision is then made based upon whether the running total corresponding to any one of the preliminary classifications exceeds a corresponding running total threshold. Both method and apparatus embodiments are disclosed. Methods are further described for determining the preliminary classifications of the detected events.

29 Claims, 10 Drawing Sheets

RUNNING TOTALS

| NORMAL | XXXXX |
|---|---|
| VF | XX |
| VT 1:1 | XXXX |
| VT NOT 1:1 | XXXXXX |
| AF | X |
| ST | XXX |

*FIG. 3*

LAST EIGHT EVENTS

| VT NOT 1:1 |
|---|
| VT NOT 1:1 |
| ST |
| VT NOT 1:1 |
| VT NOT 1:1 |
| VT NOT 1:1 |
| NORMAL |
| VT NOT 1:1 |

*FIG. 4*

RUNNING TOTALS

| NORMAL | XXXXX |
|---|---|
| VF | XX |
| VT 1:1 | XXXX |
| VT NOT 1:1 | XXXXXX |
| AF | X |
| ST | XXX |

*FIG. 5*

RUNNING TOTALS

| NORMAL | XXXXX |
|---|---|
| VF | XX |
| VT 1:1 | |
| VT NOT 1:1 | XXXXXXXXXXXX |
| AF | X |
| ST | |

*FIG. 6*

| SLIDING TOTAL THRESHOLD REACHED | CORRESPONDING REDISTRIBUTION OF RUNNING TOTALS |
|---|---|
| NORMAL SINUS RHYTHM | CLEAR THE RUNNING TOTAL BINS FOR ALL OF THE PREDETERMINED CASSIFICATION |
| VF | ADD THE COUNTS FROM THE RUNNING TOTAL BINS FOR ST, VT 1:1, AND VT NOT 1:1 TO THE RUNNING TOTAL BIN FOR VF AND THEN THEN CLEAR THE RUNNING TOTAL BINS FOR ST, VT NOT 1:1, AND AF |
| VT NOT 1:1 | ADD THE COUNTS FROM THE RUNNING TOTAL BINS FOR ST, VT 1:1, TO THE RUNNING TOTAL BIN FOR VT NOT 1:1 AND THAN CLEAR THE RUNNING TOTAL BINS FOR ST, VT 1:1 AND AF |
| VT 1:1 | ADD THE COUNTS FROM THE RUNNING TOTAL BINS FOR ST, VT NOT 1:1, AND VF TO THE RUNNING TOTAL BIN FOR VT 1:1 AND THEN CLEAR THE RUNNING TOTAL BINS FOR ST, VT NOT 1:1 VF AND AF |
| ST | ADD THE COUNTS FROM THE RUNNING TOTAL BINS FOR VT NOT 1:1, AND VF TO THE RUNNING TOTAL BIN FOR VT 1:1 AND THEN CLEAR THE RUNNING TOTAL BINS FOR VT NOT 1:1 VF AND AF |
| AF | CLEAR THE RUNNING TOTAL BINS FOR ST, VT 1:1, AND VT NOT 1:1 |

IMPLANTABLE STIMULATION DEVICE AND METHOD FOR DISCRIMINATION ATRIAL AND VENTRICULAR ARRHYTHMIAS

This application claims the benefit of U.S. Provisional Patent Application No. 60/173,526, filed Dec. 29, 1999.

FIELD OF THE INVENTION

The present invention generally relates to implantable cardiac stimulation devices, and in particular, a stimulation device capable of discriminating among various atrial and ventricular arrhythmias and delivering high voltage shocks to treat such arrhythmias.

BACKGROUND OF THE INVENTION

An ICD device is a particular type of cardiac stimulation device, which recognizes ventricular tachycardia (VT), ventricular fibrillation (VF) and other arrhythmias, and delivers high voltage electrical therapy to terminate such arrhythmias.

ICD devices have met with wide success in the detection of arrhythmias and in the administering of high voltage shocking therapy in response thereto, yet considerable room for improvement remains. In particular, many ICD recipients also suffer from supraventricular tachycardias (SVT), that is, an arrhythmia whose origin is above the ventricles and is conducted to the ventricles. The true underlying arrhythmia in these cases is often atrial fibrillation (AF), sinus tachycardia (ST), or other supraventricular tachycardias (SVTs), such as ectopic atrial tachycardia, atrial reentry, A/V nodal reentry, and paroxysmal atrial fibrillation or flutter. The SVT symptoms typically correspond to a heart rate, which is in a "low tachycardia rate" zone normally associated with VT.

These ICD patients may receive inappropriate therapy if the implanted device is not capable of reliably discriminating between VT and SVT and inappropriately classifies the rhythm as VT. It is unlikely that these arrhythmias would respond to ventricular therapy, and application of such therapy may accelerate an existing arrhythmia or induce additional arrhythmias.

ICD devices capable of dual-chamber sensing often provide better discrimination between the various types of arrhythmias than single-chamber ICD devices. However, even in dual-chamber ICD devices, it remains difficult to discriminate between VT's with 1:1 retrograde conduction (VT 1:1), and SVT's with 1:1 conduction (SVT 1:1), or ST's. Other arrhythmias that may need to be discriminated one from the other include VT's without 1:1 retrograde conduction (VT not 1:1), high rate VT's ($VT_H$), SVT's without 1:1 conduction (SVT not 1:1) and atrial flutter (AFL).

Even in circumstances where the ICD ultimately administers the correct therapy, initial errors in discriminating between the various types of arrhythmias often results in one or more intervals lapsing before therapy is administered. For example, some ICD devices discriminate between different arrhythmias by making a preliminary classification as to the type of the arrhythmia, if any, associated with each individually detected event (e.g. P-waves, R-waves, etc.) and then counting each type of event using a set of running totals. A predetermined threshold is associated with each running total. The ICD device does not make a final decision as to the type of arrhythmia until the threshold of one of the running totals is exceeded. The ICD device administers therapy appropriate to that arrhythmia.

For example, if the threshold is programmed to twenty counts and the running total for events given a preliminary classification of VT reaches twenty counts, the stimulation device identifies the arrhythmia as being a VT arrhythmia and administers appropriate therapy at that time. Unfortunately, because of the difficulty in discriminating among events associated with different types of similar arrhythmias, the wrong running total may occasionally be incremented, thereby delivering inappropriate therapy for the true underlying rhythm or delaying appropriate therapy for the underlying rhythm.

Hence, there is a need for an improved ICD device which achieves a reduction in the occurrence of inappropriate VT therapy and which provides appropriate therapy more quickly. It is to these and other ends that the invention is primarily directed.

SUMMARY OF THE INVENTION

In accordance with a first aspect of the invention, a method for use with an implantable stimulation device connected to heart tissue is provided for discriminating various arrhythmias of the heart. As used herein, the term "stimulation device" is used to cover all stimulation devices which may benefit from the use of the present invention for discriminating various arrhythmias, whether it is a pacemaker, cardioverter, defibrillator, a single-chamber or a dual chamber device, or a combination thereof.

In accordance with the method, a sequence of events are detected within the heart beginning at an initial point in time and a preliminary classification for each detected event is determined out of a plurality of heart rhythms. Running totals of the numbers of detected events within each of the predetermined classifications since the initial point in time are maintained along with sliding totals of the numbers of detected events within each of the predetermined classifications out of the most recent events. The arrhythmia of the heart is then determined based upon a combination of the running totals and the sliding totals.

In an exemplary embodiment, the implantable stimulation device is a combination ICD device which offers both atrial and ventricular pacing, and the plurality of heart rhythms includes normal sinus rhythm (NSR), ventricular fibrillation (VF), ventricular tachycardia without 1:1 retrograde conduction (VT not 1:1), ventricular tachycardia with 1:1 with retrograde conduction (VT 1:1), supraventricular tachycardias without 1:1 conduction (such as, atrial fibrillation (AF), atrial flutter (AFL), and other SVTs not 1:1) and supraventricular tachycardias with 1:1 conduction (either physiologic sinus tachycardia (ST) or a pathological SVT 1:1).

The determination of the patient's heart rhythm, based upon a combination of the running totals and the sliding totals, is performed by first determining whether the sliding total of any one of the predetermined classifications exceeds a corresponding sliding total threshold. If so, the running totals of the predetermined classifications are selectively modified. Then, a determination is made as to whether the modified running total of any one of the predetermined classifications exceeds a corresponding running total threshold and, if so, the current state of the heart is identified as being the heart state corresponding to that predetermined classification and appropriate therapy is administered.

In one specific example, the running total for VF is selectively modified as follows. If the sliding total of the number of events having a preliminary classification of VF exceeds a corresponding sliding total threshold (such as, six out of the last eight events), then the running totals for ST, VT 1:1 and VT not 1:1 are added to the running total for VF. The running totals for ST, VT 1:1, VT not 1:1 and AF are then cleared.

In the exemplary embodiment, by adding the running totals for various preliminary classifications to other preliminary classifications based upon the values of the sliding totals, the stimulation device thereby biases the running totals using the sliding totals. The specific manner by which the running totals are biased is selected to help overcome common discrimination problems occurring in stimulation devices to thereby permit the stimulation device to make a correct and final therapy decision more quickly. For example, VF events are sometimes erroneously classified as being ST events, VT 1:1 events or VT not 1:1 events. Hence, as set forth in the example, the running totals for ST, VT 1:1 and VT not 1:1 are added to the running total for VF whenever at least six of the last eight events were identified as being VF events. Thus, if such an erroneous classification occurred, it is compensated for by adding the erroneous counts to VF counts. If no such erroneous classification occurred, then even with the added counts the running total for VF will not likely exceed the corresponding threshold and erroneous therapy will not be administered.

In accordance with a second aspect of the invention, a method is provided for use with an implantable stimulation device connected to heart tissue for determining a classification for an event detected within the heart, wherein the heart rate is between an upper and lower predetermined heart rate threshold, and wherein the heart is in atrial/ventricular (AN) synchrony. Initially, if a P-R interval (associated with the event) is detected, then a determination is made as to whether the P-R interval is physiologic, that is, between a physiologic upper and lower predetermined P-R interval thresholds. If the P-R interval is not between the upper and lower predetermined P-R interval thresholds, then the event is identified as being associated with VT 1:1. If, however, the P-R interval is between the upper and lower predetermined P-R interval thresholds, then a further determination is made as to whether the P-R interval is stable. If the P-R interval is not stable, then the event is identified as being associated with VT 1:1. If the P-R interval is stable, the event is either ST or SVT 1:1 and receives a preliminary classification of "ST" (As used here and in the flowcharts, the designation of "ST" is arbitrary and intended to include both physiological sinus tachycardias and all other pathological supraventricular tachycardias which have 1:1 conduction, since in a ventricular shocking device, if either one is present, no therapy is provided. However, in one embodiment, additional discriminators could be added to distinguish between a physiological ST and a pathological SVT 1:1 and the device could further provide atrial shock therapy.).

Among other advantages, by evaluating whether the P-R interval is physiologic and by evaluating the stability of the P-R intervals, the implantable stimulation device is better able to discriminate between VT 1:1 arrhythmias and ST or SVT 1:1 arrhythmias.

This method for determining a classification for an event may be advantageously employed as part of the determination of the preliminary classification of events detected within the heart for use with the first aspect of the invention.

In accordance with a third aspect of the invention, a method is provided for use with an implantable stimulation device connected to heart tissue for determining a classification for an event detected within the heart, wherein the heart rate is detected between an upper and a lower predetermined heart rate threshold, but wherein the heart is not in AV synchrony. Initially, an atrial rate and a ventricular rate are detected. A determination is made as to whether the atrial rate exceeds the ventricular rate, and if it does not, the event is identified as being associated with VT not 1:1. However, if the atrial rate does exceed the ventricular rate, then a determination is made as to whether an R-R interval associated with the event is stable. If the R-R interval is not stable, the event is either atrial fibrillation (AF), atrial flutter (AFL) or SVT not 1:1 and receives a preliminary classification of "AF". (The designation of "AF", as used here and in the flowcharts, is arbitrary and intended to include atrial fibrillation and atrial flutter and all other supraventricular tachycardias without 1:1 conduction, since in a ventricular only shocking device, no therapy is provided. However, in one embodiment, additional discriminators could be added to distinguish between atrial fibrillation from atrial flutter and other SVTs not 1:1, and the device could further provide atrial shock therapy.)

If, however, the R-R interval is stable, a further determination is made as to whether an R-P interval associated with the event is stable. If the R-P interval is not stable, the event is both AF and VT not 1:1 and receives a preliminary classification of VT not 1:1. (In this instance, in a ventricular shocking device, you would treat the VT. However, in a device, which also provides atrial therapy, the priority would be to treat the VT first, wait to see if the AF also resolves and, if it does not, then treat the AF.).

If, however, the R-P interval is stable, the event is AF, AFL or SVT not 1:1 and receives a preliminary classification of AF. (Again, in a ventricular shocking device, the designation of AF is arbitrary since in each case (AF, or SVT not 1:1), no therapy is provided.) Among other advantages, by evaluating the stability of the R-R and the R-P intervals, the implantable stimulation device is better able to discriminate VT not 1:1 arrhythmias from supraventricular tachycardias such as atrial fibrillation (AF), atrial flutter (AFL), and other supraventricular tachycardias that do not have 1:1 conduction (SVT not 1:1).

This method for determining a classification for an event also may be advantageously employed as part of the determination of the preliminary classification of events detected within the heart for use with the first aspect of the invention.

Other objects and advantages of the invention are achieved as well. Apparatus embodiments of the invention are also provided.

BRIEF DESCRIPTION OF THE DRAWINGS

The above and other aspects, features and advantages of the present invention will be more apparent from the following more particular description thereof, presented in conjunction with the following drawings wherein:

FIG. 3 is a graphic illustration of an exemplary set of bins used in connection with maintaining running totals while performing the method of FIG. 2;

FIG. 4 is a graphic illustration of an exemplary set of most recent events used in maintaining sliding totals while performing connection with the method of FIG. 2;

FIG. 5 provides a graphic illustration of an example of a set of running totals before redistribution, and further showing the step of redistributing events using arrows, performed in accordance with the method of FIG. 2;

FIG. 6 provides a graphic illustration of the final redistribution of events for the example shown in FIG. 4; FIG. 13 sets forth a table identifying the particular redistribution of the running bin totals for each preliminary classification.

DETAILED DESCRIPTION OF THE INVENTION

The present invention relates to improved techniques for discriminating among various types of arrhythmias using an implantable stimulation device. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
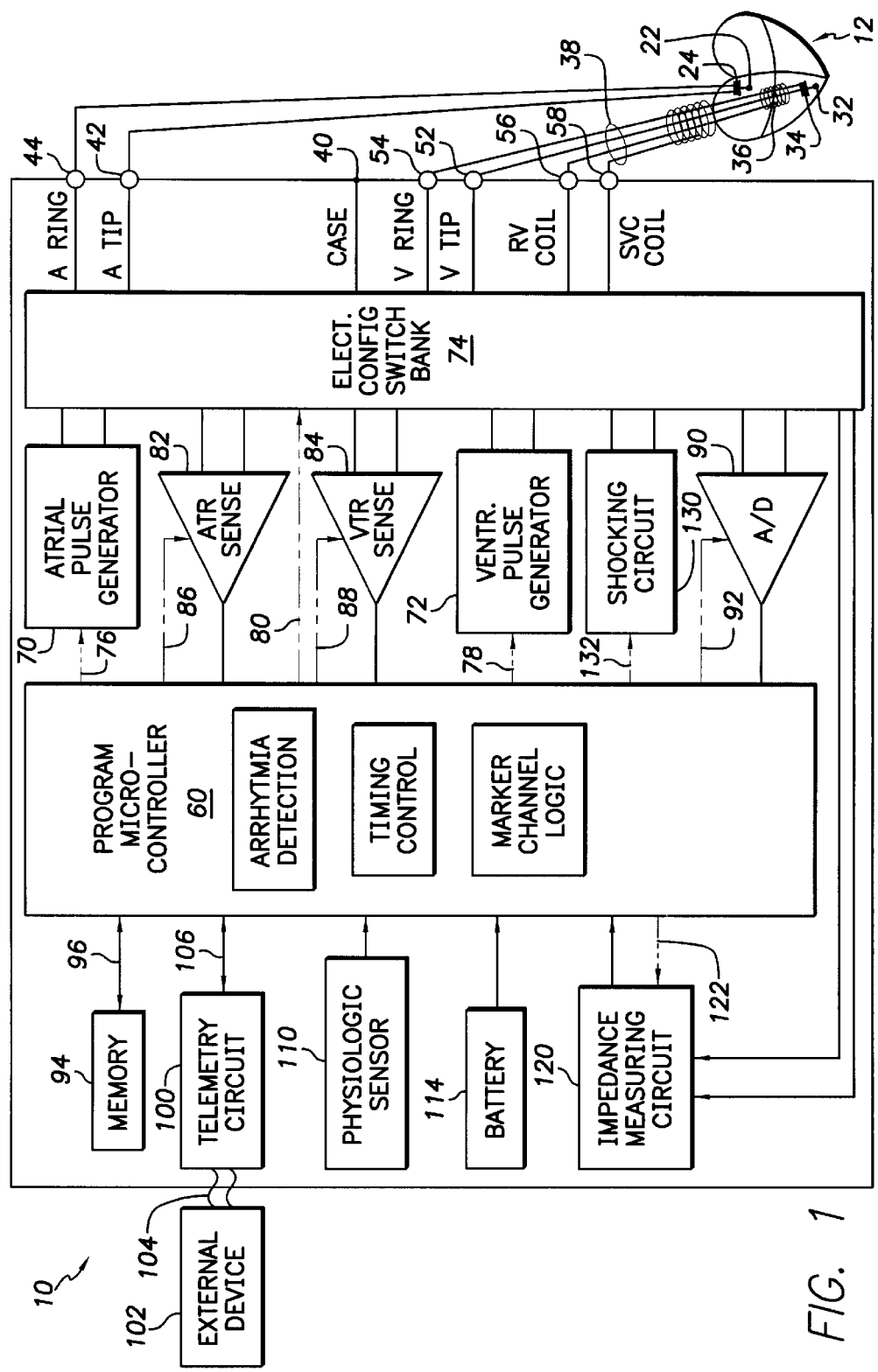
FIG. 1 is a functional block diagram of a dual-chamber implantable stimulation device illustrating the basic elements of a stimulation device which can provide cardioversion, defibrillation and dual-chamber sensing and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/196,898 (Pianca et. al), and U.S. Pat. No. 5,466,254 (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses (e.g., rate and AV-Delay), as well as keeping track of the timing of any refractory periods, PVARP intervals, noise detection windows, evoked response windows, alert intervals, marker channel timing, watch-dog or safety timers, etc., as is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. For a complete description of a typical sense amplifier, see U.S. Pat. No. 5,573,550 (Zadeh et. al). For a complete description of an automatic gain control system, see U.S. Pat. No. 5,685,315 (McClure et. al). Accordingly, the '550 and the '315 patents are hereby incorporated herein by reference.

The outputs of the atrial and ventricular sense amplifiers, 82 and 84, are connected to the microcontroller 60, which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 86, as is known in the art.

For arrhythmia detection, the present invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104. For examples of such devices, see U.S. Pat. Nos. 4,809,697 (Causey, III et al.) and 4,944,299 (Silvian), which patents are hereby incorporated herein by reference.

In the preferred embodiment, the stimulation device 10 further includes a physiologic sensor 110. The physiological sensor 110 is used to detect the exercise state of the patient, to which the microcontroller 60 responds by adjusting the rate and AV Delay at which the atrial and ventricular pulse generators, 70 and 72, generate-stimulation pulses. Such sensors are commonly called "rate-responsive" sensors. The type of sensor used is not critical to the present invention and is shown only for completeness.

The stimulation device additionally includes: a battery 114, which provides operating power to all of the circuits shown in FIG. 1. For the stimulation device 10, which employs shocking therapy, the battery must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 114 must also have a predictable discharge characteristic so that elective replacement time can be detected. Accordingly, the present invention employs lithium/silver vanadium oxide batteries, as is true for most (if not all) such devices to date.

As further shown in FIG. 1, the present invention preferably includes an impedance measuring circuit 120 which is enabled by the microcontroller 60 by a control signal 122. The impedance measuring circuit 120 is not critical to the present invention and is shown for only completeness.

It is the primary function of the present invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
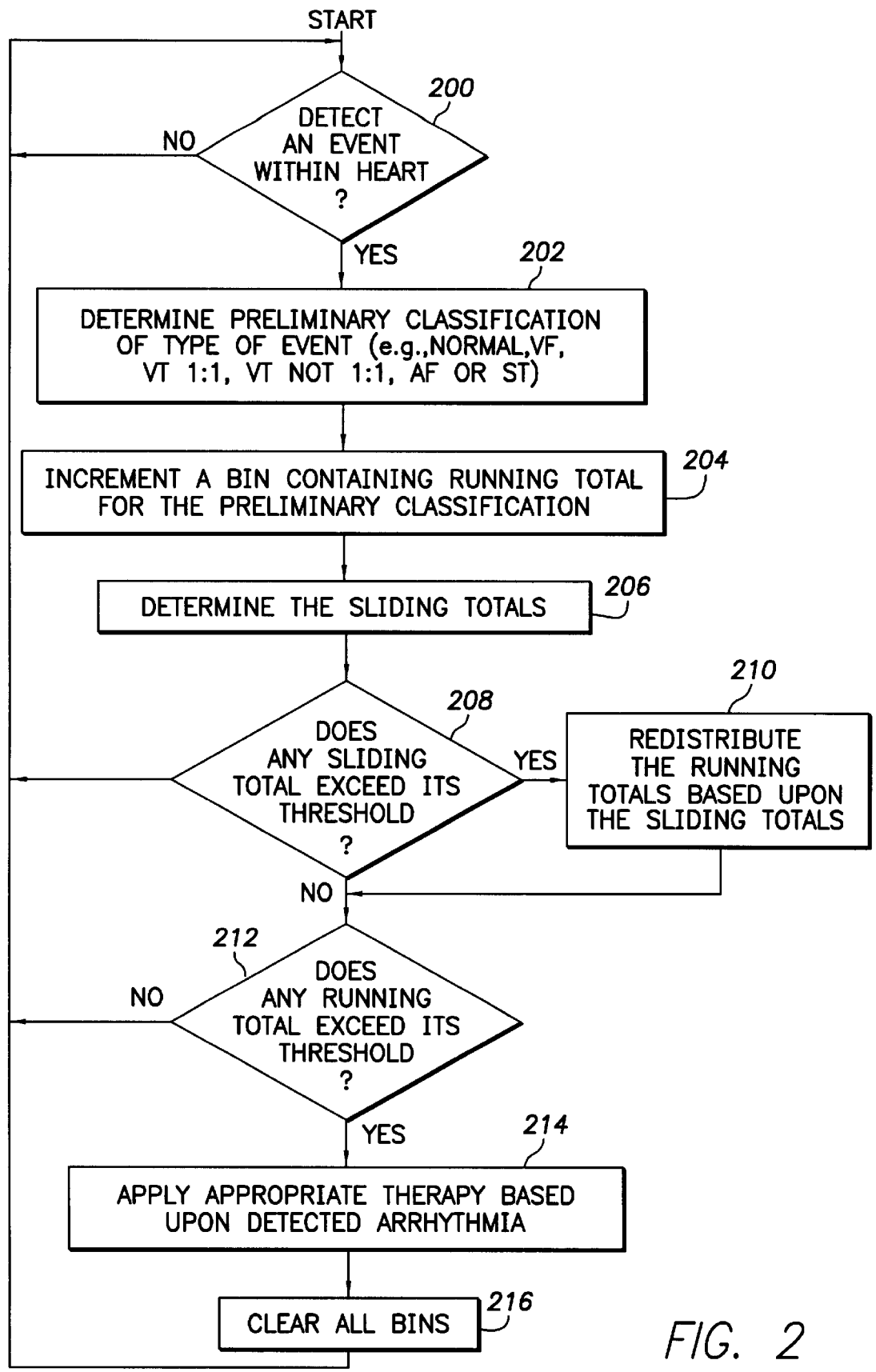
FIG. 2 is a high-level flow chart illustrating a method for determining an arrhythmia, if any, of a patient in which the stimulation device of FIG. 1 is implanted.

In FIG. 2, a flow chart is shown describing an overview of the operation of the novel features of the present invention. In FIGS. 7–12, a preferred method for discriminating among various types of arrhythmias will be summarized, wherein the flow charts are connected to each other by the designators A, B, C, etc. In these flow charts, the various algorithmic steps are summarized in individual "blocks" or "steps". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the'stimulation device. Those skilled in the art may readily write such a control program based on the flow charts and other descriptions presented herein.

In FIG. 2, at step 200, an electrical event is detected within the heart. At step 202, a preliminary determination is made of the type of event based upon a beat-by-beat analysis resulting in a preliminary classification which identifies the event as either corresponding to a normal heart rhythm (NSR), or to a VF, VT 1:1, VT not 1:1, AF or ST arrhythmia. A particular technique for making the preliminary classification of the each event will be described in detail below with reference to FIGS. 3–12. However, other specific techniques may alternatively be employed (e.g., rate zone detection, sudden onset, stability, morphology discrimination, etc). In general, any technique capable of the providing a preliminary classification of the various types of arrhythmias may be employed. At step 204, a bin containing the "running total" for the preliminary classification is incremented. That is, the "running total" represents the number of events of a particular type detected since an initial point in time.

An exemplary set of bins is illustrated in FIG. 3. As can be seen, a separate bin for each of the six types of arrhythmias is provided. Each of the bins includes one or more counts. It should be understood, however, that during the first iteration of the method of FIG. 2, only a single one of the bins is incremented by a single count. Hence, the example of FIG. 3 illustrates the bins as they might appear after the method of FIG. 2 has been repeated in a loop several times.

Continuing with the description of FIG. 2, at step 206, the stimulation device determines the number of events of each type occurring within the last N events to produce a set of "sliding totals" for the events. Hence, a sliding total is defined as the number of events of a particular type detected within the last N events, wherein N is a predetermined value. In other words, to determine the "set" of sliding totals, the stimulation device determines the number of the events corresponding to a normal sinus rhythm occurring within the last N events, then determines the number of the events corresponding to VF within the last N events, and so forth for each of the event types, etc. In one example, N is set to eight.

FIG. 4 graphically illustrates an example of a sequence of eight previous events. As can be seen, six of the eight events were given a preliminary classification of VT not 1:1. One of the events was given a preliminary classification of ST. The remaining event was given a preliminary classification of a normal sinus rhythm. Hence, in the example of FIG. 4, the sliding total for VT not 1:1 is six; the sliding total for ST is one; and the sliding total for normal sinus rhythm is also one. As with the example of FIG. 3, the example of FIG. 4 illustrates a running total sequence as it might appear after the method of FIG. 2 has been repeated in a loop several times.

The stimulation device maintains a separate threshold for each type of event corresponding to the sliding totals. At step 208, the stimulation device determines whether any one of the sliding totals has exceeded its respective threshold. For example, the threshold for VT not 1:1 may be set to six out of eight. Accordingly, at step 208, the stimulation device determines whether the number of events given a preliminary classification of VT not 1:1 has reached the threshold of six out of eight. For simplicity, in the illustrated implementation, each sliding total threshold is set to the same value (i.e., the threshold for normal sinus rhythm, VF, VT 1:1, VT not 1:1, etc. are all set to six out of eight). In other implementations, each different preliminary classification may have a different threshold (e.g., some may be set to five out of eight, whereas others may be set to seven out of eight).

If one of the sliding total thresholds has been reached, then execution proceeds to step 210 (FIG. 2) wherein the stimulation device selectively redistributes, or otherwise modifies, counts within the bins containing the running totals (i.e., the bins shown in FIG. 3) based upon the classification of the sliding total found to have exceeded its respective threshold. FIG. 13 sets forth the particular redistribution of the bin totals for each preliminary classification. In the example of FIG. 4, the threshold for VT not 1:1 has been reached because at least six of the eight entries correspond to VT not 1:1.

Accordingly, FIGS. 5 and 6 illustrate a resulting redistribution of the running total bins. As such, the stimulation device operates to move all of the counts found in the bins for VT 1:1 and ST into the running total bin for VT not 1:1 (i.e., per the rules set forth in FIG. 13). The resulting redistributed bin counts are shown in FIG. 6. As noted above in the Summary of the Invention, by adding the running totals for various preliminary classification bins to other preliminary classification bins based upon the values of the sliding totals, the stimulation device biases the running totals so as to help overcome common discrimination problems occurring in stimulation devices, thereby permitting the stimulation device to make a more correct decision regarding the type of therapy, if any, to be administered and to reach the decision more quickly. In this regard, the redistribution functions set forth in FIG. 13 have been selected so as to overcome likely discrimination problems. In other embodiments, other particular redistribution functions may be performed, perhaps to account for other discrimination problems.

One rationale for the redistribution performed at step 210 (FIG. 2) is as follows. The heart is typically in only one state of arrhythmia at any one time. Hence, if some closely spaced events received differing classifications, classification errors have likely occurred. To correct the errors, the stimulation device looks to the most recent events that have been classified to determine whether there is a large group of similarly classified events, and if so the stimulation device biases its final decision in favor of that classification. Hence, if six out of eight events all have the same classification, the stimulation device concludes that the other recent classifications are probably incorrect and reclassifies those counts accordingly. Reclassification is achieved by redistributing the running total bins as already described. However, because the six events in the sliding totals may actually have been the erroneously classified events, the stimulation device does not administer therapy immediately. Rather the stimulation device still waits until a running total threshold has been met before administering therapy.

Referring back to FIG. 2, at step 212, the stimulation device determines whether any one of the running totals now exceeds its respective threshold. If none of the running totals were found to have exceeded their respective thresholds, then execution returns to step 200 for detection of the next heart event.

However, if one of the running totals does exceed its respective threshold at step 212, then the stimulation device administers therapy appropriate to the particular arrhythmia at step 214, corresponding to the arrhythmia whose running total bin was found to have exceeded its respective threshold. Hence, in the example of FIG. 6, wherein the bin threshold for VT not 1:1 was exceeded, therapy appropriate to the VT not 1:1 arrhythmia is administered by the stimulation device.

Thereafter, step 216 is performed wherein all running total bins and all sliding totals are cleared. Then, execution returns to step 200 to detect the next event within the heart. In any case, execution continues in a loop to constantly monitor the state of a heart and administer therapy whenever necessary.

With reference to FIGS. 7–12, a specific method for discriminating among various types of arrhythmias using a stimulation device will now be described.

Initially, at step 300, the stimulation device senses a cardiac event. As determined at step 302, if the event is not a ventricular event, then it is atrial in origin and the stimulation device computes any P-P interval at step 304 and returns to step 300 to await detection of another cardiac event.

If the next cardiac event is a ventricular event, then at step 306 the stimulation device computes the R-R, P-R and R-P intervals and a moving average for the R-R interval (AVG R-R) based, for example upon the last four R-R intervals that have been sensed, and a moving average for the P-R interval (AVG P-R) based, for example, upon the last four P-R intervals that have been sensed. Of course, if fewer than four R-R or P-R intervals have been sensed, then the moving average is based upon only those intervals that have already been sensed.

At step 310, the stimulation device determines whether the last R-R interval exceeds the last P-R interval. If not, then the event is identified as being a premature ventricular contraction (PVC), and a PVC counter is incremented at step 311, then execution continues at step 312. Otherwise, execution proceeds directly to step 312, wherein the stimulation device determines whether the average R-R interval is greater than an interval associated with a predetermined lower VT rate threshold, for example, of 120 beats per minute (bpm).

If the average R-R interval was determined, in step 312, to have a corresponding ventricular rate that was below the VT rate threshold, then the stimulation device concludes that the event was a normal sinus rhythm event. Execution then proceeds to step 314 where the stimulation device determines whether a 1:1 P-R association exists. If so, then the normal sinus P-R interval (NSPR) value is averaged using a weighted average at step 315, such as, NSPR=0.75 times the previous NSPR+0.25 times the average P-R interval (AVG P-R), i.e. the latter term being the average P-R value determined in step 306. The NSPR value is updated in this manner to reflect the stable normal sinus rhythm P-R interval. This is a weighted moving average where the current P-R interval contributes 25% to the moving average. If 1:1 P-R association is not found, then a new value for the NSPR is not calculated. In any case, execution proceeds to step 316, wherein a running total bin for normal sinus rhythm is incremented.

However, if the average R-R interval was determined, at step 312, to have a corresponding ventricular rate that is greater than the lower VT rate threshold, then the event is likely associated with some type of arrhythmia and steps are taken to begin identifying the preliminary classification for the arrhythmia.

To this end, the stimulation device computes an upper limit for the P-R interval (PR UL) value, at step 318, where PR UL is set to a value slightly higher than the normal sinus P-R interval (NSPR), e.g., equal to 17/16 times the NSPR, wherein the value for the NSPR is calculated in step 315 as a percentage of the previous NSPR plus a percentage of the average P-R interval (AVG P-R). The PR UL value is later used in the determination (step 334 in FIG. 8) of whether the P-R interval is physiologic or due to retrograde conduction. A typical NSPR value is 200 ms. The value 17/16 is chosen because is can be readily computed with 4 shifts and one add instruction without multiplication or division, however, other values that are slightly greater than 1 would also work.

In order not to prolong detection, a high rate safety timer is also employed in the present invention. Prolonged detection may occur when rhythm cycle lengths occur in more than one zone, for example, between VT and VF. The timer is started when a potentially sustained tachyarrhythmia is initially declared, and therapy is delivered whenever it times-out. To this end, the microcontroller 60 initializes a high rate safety timer (not shown), HRST, in step 318 in FIG. 7.

Figure 8:
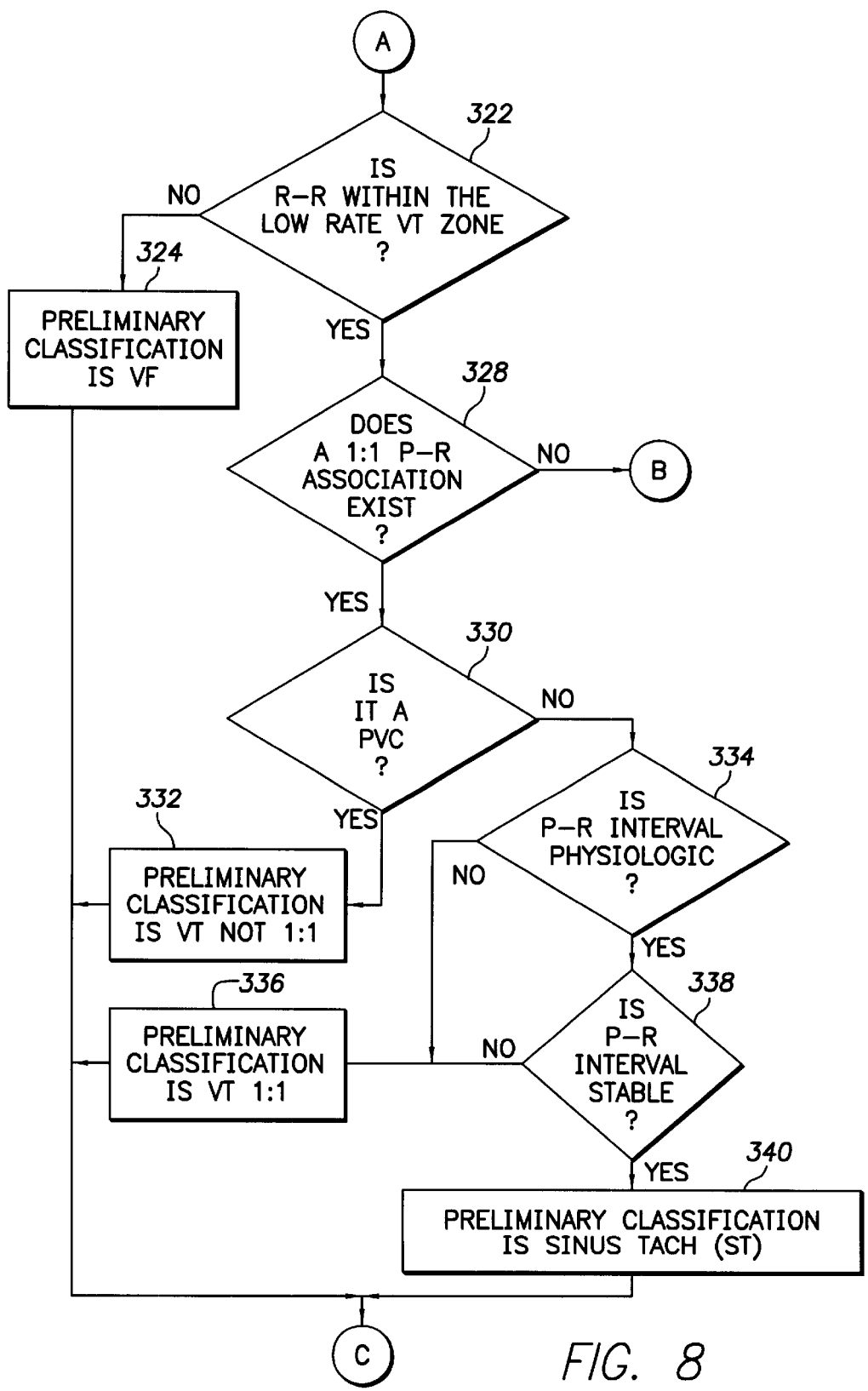
Figure 9:
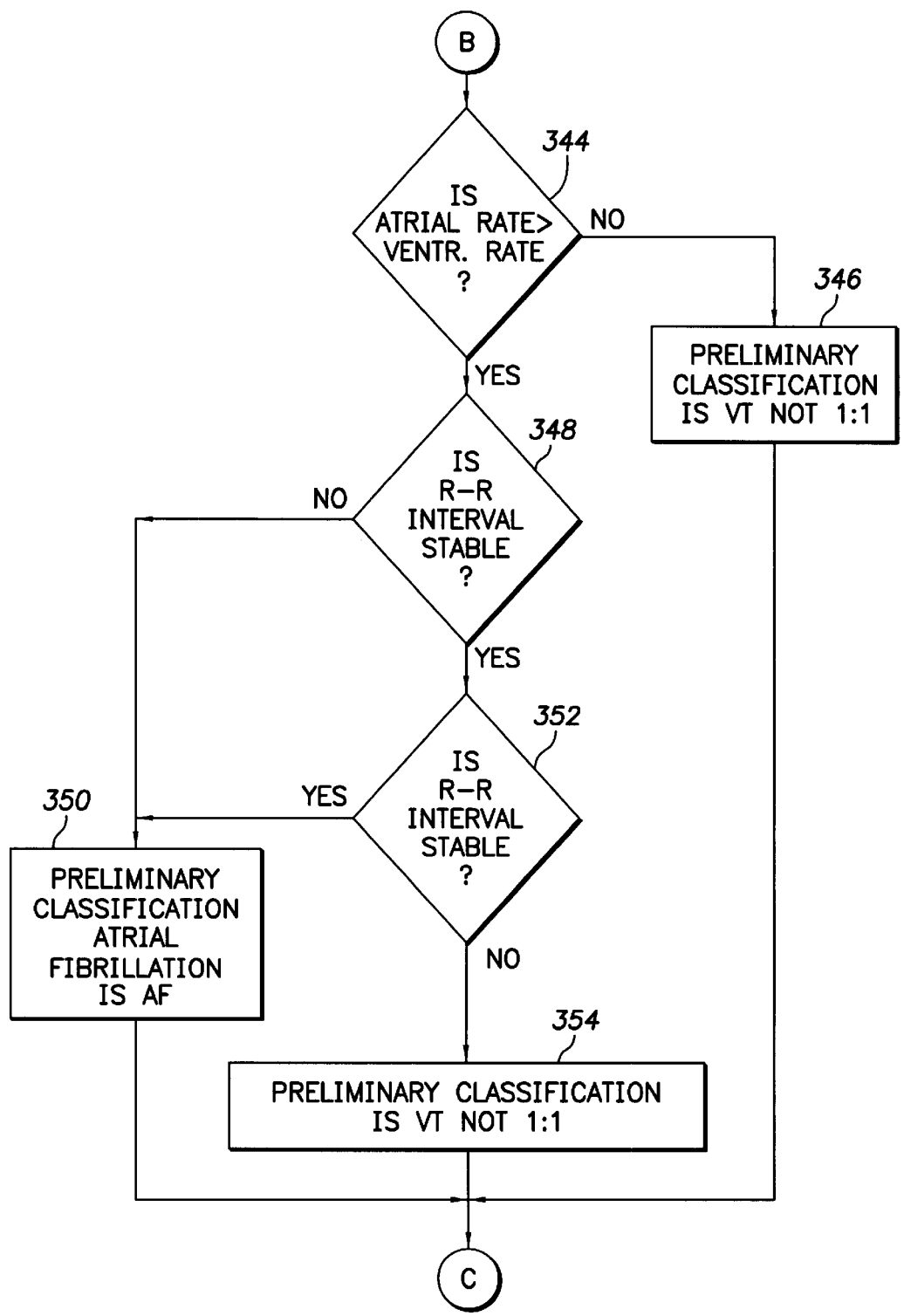

Thereafter, the stimulation device executes the preliminary classification sub-method illustrated in FIGS. 8 and 9 to classify the type of arrhythmia associated with the event. The preliminary classification sub-method is also referred to herein as a "beat-by-beat" method.

Referring first to FIG. 8, at step 322 the stimulation device determines whether the current R-R interval has a corresponding ventricular heart rate that falls within a Low Rate VT Zone (e.g., corresponding to a zone defined by the limits, for example, 120 and 180 bpm). If the heart rate is not within that Low Rate VT Zone, then the arrhythmia is either a high rate ventricular tachycardia ($VT_H$) or a ventricular fibrillation (VF). (The assumption that the heart rate is above the Low Rate VT Zone is valid because the ventricular rate, as determined by the average R-R interval, was previously determined to be greater than the lower VT rate threshold at step 312 of FIG. 7.) For simplicity, $VT_H$ is assumed to need the same therapy as VF. Accordingly, the stimulation device makes a preliminary classification of VF at step 324, however, one of skill in the art could readily add a High Rate VT Zone and another bin for a preliminary classification of High Rate VT. Then, control goes to "C" in FIG. 10 for further analysis, as will be described later on.

If the R-R interval has a corresponding ventricular heart rate that falls within the Low Rate VT Zone, at step 322, the stimulation device then must discriminate among various other possible arrhythmias including a high ventricular rate without 1:1 AV association (VT not 1:1), a high ventricular rate with 1:1 AV association typically due to retrograde conduction (VT 1:1), a supraventricular tachycardia (SVT) with 1:1 conduction, such as, a sinus tachycardia (ST), or an SVT without 1:1 conduction, such as, atrial fibrillation (AF), atrial flutter (AFL), etc.

To achieve the necessary discrimination, the stimulation device initially determines whether there is a 1:1 P-R association at step 328. If so, then, at step 330, the stimulation device takes into account whether the event is a PVC as determined previously at step 311 of FIG. 7. If the event is a PVC event, then the stimulation device makes a preliminary classification of the sensed ventricular event as being associated with a VT not 1:1 arrhythmia at step 332.

If the event was not a PVC, the event may be associated with VT 1:1. However, the stimulation device must account for the possibility that the arrhythmia is an ST or an SVT 1:1 rather than a VT 1:1. To this end, the stimulation device further determines whether the P-R interval is physiologic at step 334. By "physiologic", it is meant that the P-R interval is neither to short nor too long as determined by predetermined cutoff values set to, for example, greater than the upper limit for the P-R interval (PR UL) or less than (PR UL)/4.

If the P-R interval is not physiologic, then the arrhythmia could still be either a VT 1:1 or an SVT 1:1. If no other discriminators are available, for safety reasons, the stimulation device assumes that the arrhythmia is VT 1:1 rather than SVT 1:1 and sets the preliminary classification to VT.

If other discriminators are available (e.g., sudden onset or morphology), then it is within the scope of the present invention to be modified to use such discriminators for further classifying the cardiac events as a physiological sinus tachycardia, ST, or a pathological SVT 1:1. In which case, if ST was present, the device would continue monitoring, since no therapy is needed. And if SVT 1:1 was present, a ventricular shocking device would still treat the arrhythmia with ventricular shock therapy because the patient would otherwise continue to have poor hemodynamics. But, if an atrial shocking device (or a dual shocking device) was implanted, then the device preferably would attempt to treat the SVT 1:1 with atrial shock therapy. The use of sudden onset is well known in the art to detect abrupt changes in rate as the signature for a true tachycardia, and a slow onset corresponding to a heart rhythm responding to exercise. Alternatively, the physiologic sensor 110 may be used to detect the exercise state of the patient, which is well known in the art. For a complete description of a system capable of morphology discrimination, see U.S. Pat. Nos. 5,240,009 (Williams) and 5,779,645 (Olson et. al), which patents are hereby incorporated herein by reference.

If, at step 334, the P-R interval was found to be physiologic, then the stimulation device further determines whether the P-R intervals are stable at step 338. Stability is determined by any of a variety of suitable methods, such as by comparing various recent P-R intervals with each other to determine the average variance therebetween. If the variance exceeds a predetermined value, then the P-R intervals are deemed to be not stable and, if so, the stimulation device sets the preliminary classification for the sensed ventricular event as being VT 1:1, at step 336. If the P-R intervals are stable, then the arrhythmia is either a sinus tachycardia (ST) or a supraventricular tachycardia (SVT 1:1). In a ventricular shocking device, no further discrimination is necessary between ST and SVT 1:1, as both require no therapy. (However, in a stimulation device with atrial shocking therapy, other discriminators (such as, morphology of the atrial signal, timing between the right and left atrial signals, or detection of the "sequence of activation") can further classify ST from SVT 1:1, as described above.) As such, the stimulation device arbitrarily sets the preliminary classification as being sinus tachycardia (ST) at step 340. Thus, by evaluating whether the P-R interval is physiologic and by evaluating the stability of the P-R intervals, the. stimulation device is able to discriminate between VT 1:1 arrhythmias and ST arrhythmias.

Referring again to FIG. 8, if the stimulation device determined that there was not a 1:1 correlation between P and R at step 328, then control goes to FIG. 9, wherein the stimulation device further determines whether the atrial rate exceeds the ventricular rate at step 344. If the atrial rate does not exceed the ventricular rate, then the stimulation device makes a preliminary classification as being VT not 1:1 at step 346.

If, however, the atrial rate does exceed the ventricular rate, then the stimulation device must account for the possibility that the arrhythmia is an SVT without a 1:1 P-R association (such as AF, AFL or other SVT not 1:1), rather than, or in addition to, a VT not 1:1. To this end, the stimulation device then further determines whether the R-R intervals are stable at step 348. If not stable, then the arrhythmia is one of AF, AFL or SVT not 1:1 arrhythmia.

Likewise, if the R-R intervals are stable at step 348, then the stimulation device further determines whether the R-P intervals are stable at step 352 and, if so, then the arrhythmia is also one of AF, AFL or SVT not 1:1 arrhythmia.

Since the present embodiment is a ventricular stimulation device, further discrimination between AF, AFL, or SVT not 1:1 is not necessary as they require no therapy. However, for an atrial therapy stimulation device, rate, stability of the P-P interval, sudden onset, and the morphology of the P-wave can further discriminate to determine the appropriate therapy. As such, if the arrhythmia is one of AF, AFL or SVT not 1:1, then the stimulation device arbitrarily sets the preliminary classification as being atrial fibrillation (AF) at step 350.

If the R-P intervals are not stable, then the arrhythmia includes both AF and a VT not 1:1. Since the device of the present invention is designed to treat ventricular arrhythmias, the stimulation device makes a preliminary classification as being a VT not 1:1 arrhythmia at step 354.

Thus, the sub-method of FIGS. 8 and 9 operates to identify a preliminary classification of the heart arrhythmia associated with the most recently detected ventricular event. The classifications are merely preliminary and, as will be seen with reference to the remaining steps of FIGS. 10 and 12, the stimulation device uses the preliminary classification in conjunction with other information to formulate a final decision as to the current arrhythmia, if any, prior to administering any therapy.

The final output of the classification sub-method of the FIGS. 8 and 9 is a "code" corresponding to one of the preliminary classifications (VF, VT not 1:1, VT 1:1, ST or AF).

Figure 10:
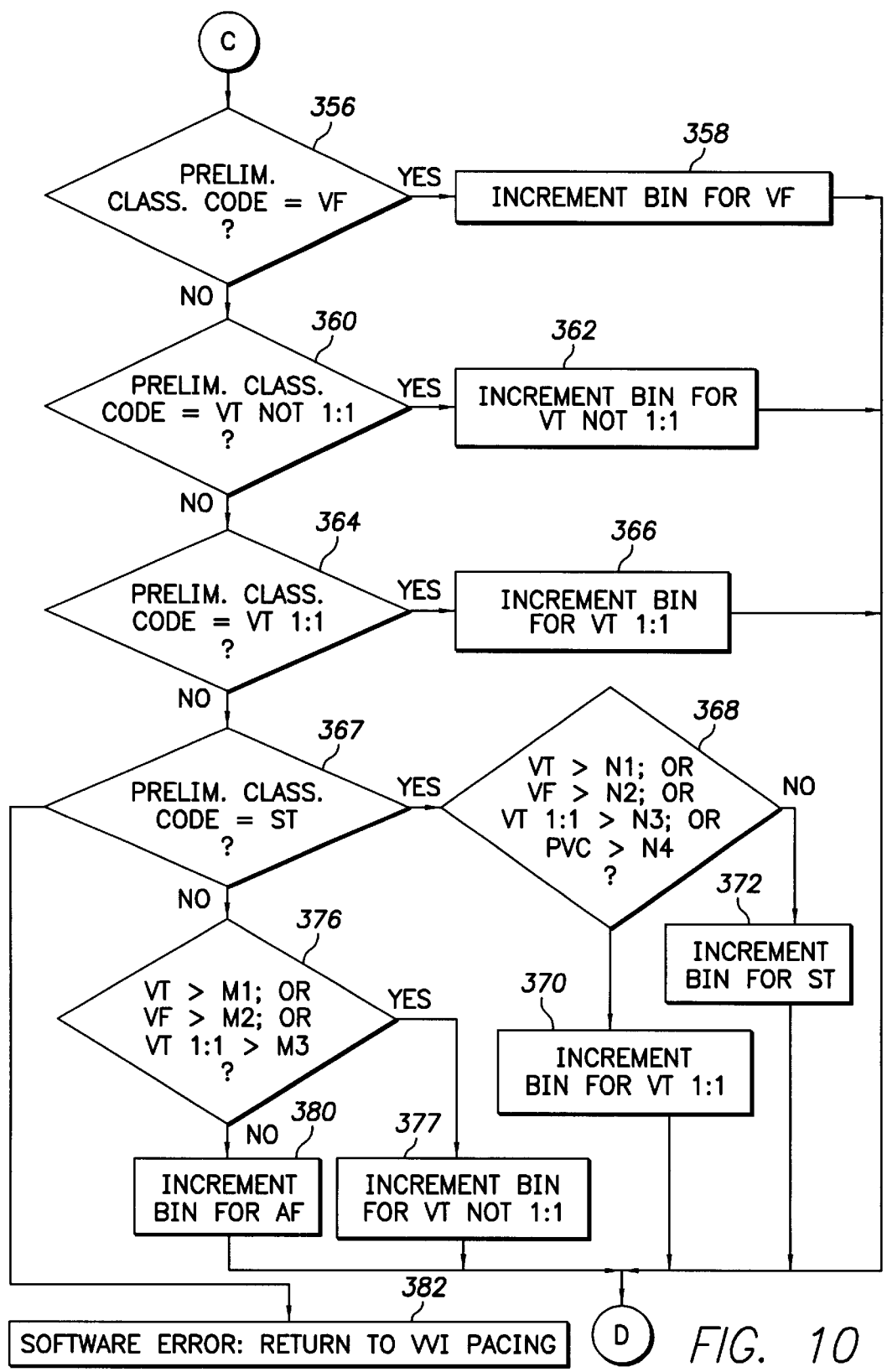
Figure 11:
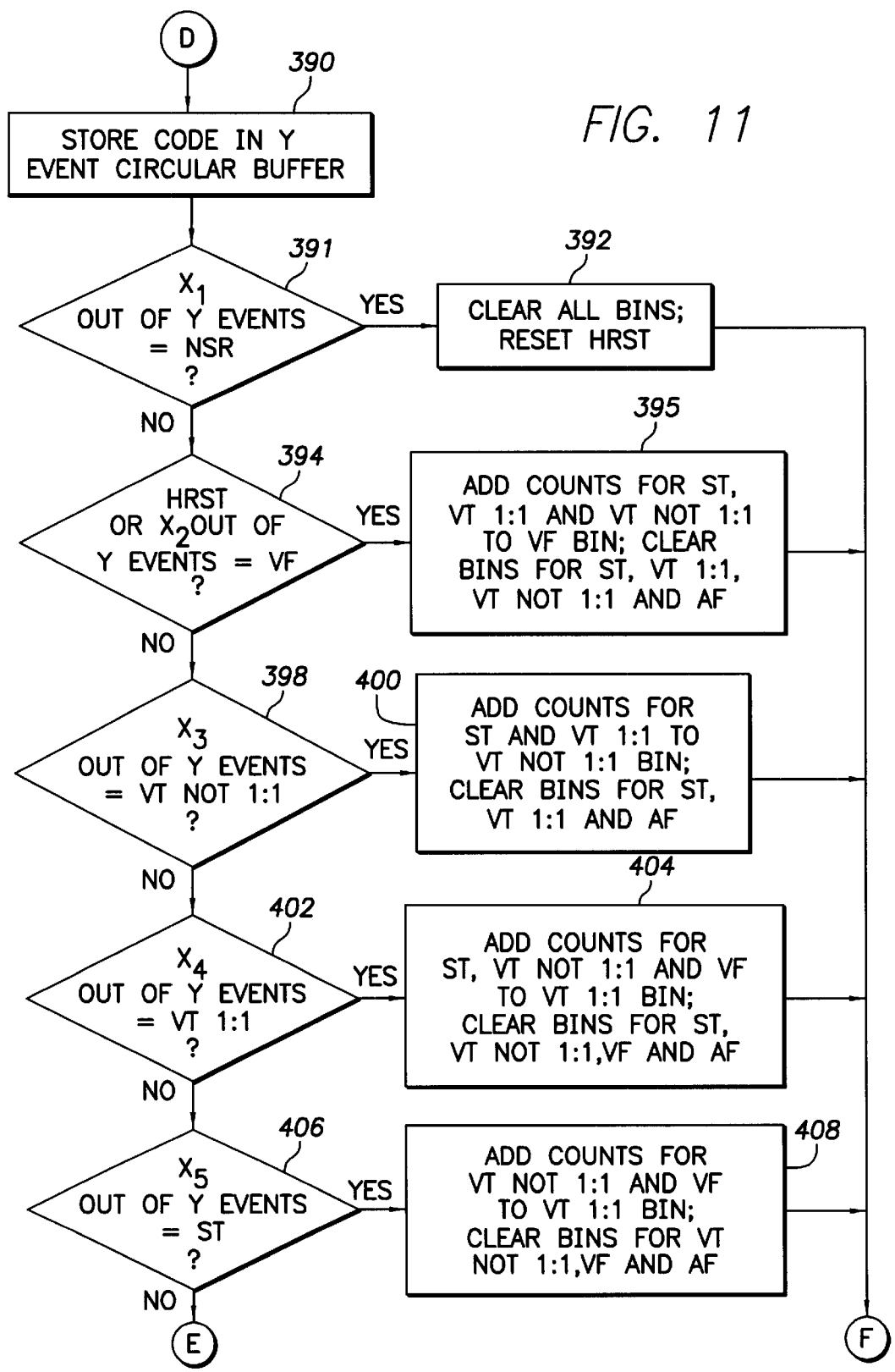
Figure 12:
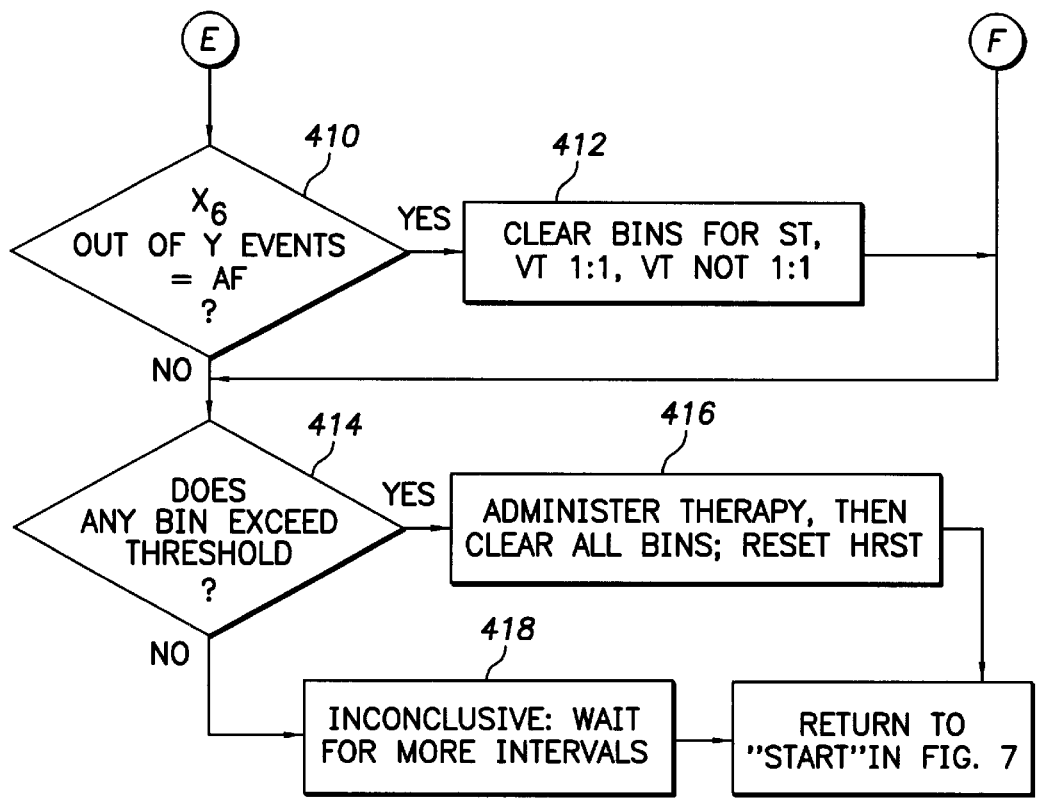

Referring now to FIG. 10, at step 356, if the preliminary classification code from FIG. 8 was set to VF, then a VF running total bin is incremented at step 358. If the preliminary classification code was set to VT not 1:1 as determined at step 360, then a VT not 1:1 running total bin is incremented at step 362. If the preliminary classification code was set to VT 1:1 as determined at step 364, then the VT 1:1 bin is incremented at step 366.

However, if the preliminary classification code was set to sinus tachycardia, ST, as determined at step 367, the stimulation device further determines, at step 368, whether additional selected criteria has been met to distinguish between ST and VT 1:1. For example, step 368 determines whether any of the last eight events included more that $N_1$ VT events, or more that $N_2$ VF events, more than $N_3$ VT 1:1 events, or more than $N_4$ PVC events (wherein $N_1$, $N_2$ and $N_3$=2 or more events and preferably 3 or 4, and $N_4$=1 or more). If so, then the stimulation device concludes that the event is a ventricular arrhythmia onset and, for safety, increments the VT not 1:1 running total bin at step 370. If not, the stimulation device increments an ST running total bin at step 372.

If the preliminary classification code was not ST (as determined at step 367), then execution proceeds to step 374 where the stimulation device determines whether the preliminary classification code was set to AF. The stimulation device further determines at step 376 whether additional selected criteria has been met to distinguish between AF and VT not 1:1. For example, step 376 determines whether any of the last eight events included more that $M_1$ VT events, or more that $M_2$ VF events, or more than $M_3$ VT 1:1 events (wherein $M_1$, $M_2$ and $M_3$=2 or more events and preferably 3 or 4). If so, the stimulation device concludes that the event is an onset of a ventricular arrhythmia and, for safety, increments the VT not 1:1 bin at step 377. If not, the stimulation device concludes the event was either AF or AFL and increments the AF bin at step 380. (There is no separate AFL bin because discrimination between AF and AFL is unnecessary. In both cases ventricular therapy is withheld.)

At step 374, if the preliminary classification code was found to not have been set to AF, then the stimulation device concludes that a software error must have occurred since the event was therefore not identified as being any of the permissible preliminary classifications. In response, at step 382, the stimulation device initiates a VVI sensing method and abandons the method described in FIGS. 7–10. The VVI method may be entirely conventional and is therefore not described herein.

The steps thus far described in FIGS. 7–10 operate to increment one of the various running total bins for each sensed ventricular event based upon the preliminary classification of the event in conjunction with other information. In each case, execution ultimately proceeds to FIGS. 11–12 at step 390 wherein a preliminary classification code value corresponding to the just-incremented bin is added to a sliding total circular buffer containing Y values. The value for Y may be set to, for example, eight. Thereafter, a sequence of steps are performed which serve to redistribute the running total bins based upon an analysis of the relative numbers of different preliminary classification code values stored within the circular buffer. More specifically, a separate threshold value ($X_1$ through $X_6$) is set for each type of preliminary classification code value stored within the circular buffer. If the threshold is exceeded for any one preliminary classification code value, then a corresponding re-distribution of mutually conclusive events is performed. With Y set to eight, the threshold values ($X_1$ through $X_6$) are all, preferably, set to six.

The redistribution steps proceed as follows. At step 391 the stimulation device determines whether at least X, of the preliminary classification codes for the last Y events within the circular buffer are set to normal sinus rhythm (i.e., X, out of Y events=NSR?) and, if so, the stimulation device concludes that the heart is operating under a normal sinus rhythm and all bins are cleared and the high rate safety timer (HRST) is reset at step 392.

At step 394, the stimulation device determines whether at least $X_2$ of the last Y events in the circular buffer are set to VF and, if so, step 395 is performed wherein the bins are redistributed, in accordance with FIG. 13, to add the counts within the ST, VT 1:1 and VT not 1:1 bins to the VF bin. The ST, VT 1:1, VT not 1:1, and AF bins are then all cleared. The redistribution is performed to account for the possibility that some VF events were erroneously given a preliminary classification of either ST, VT 1:1, VT not 1:1 or AF.

Alternatively, if the high rate safety timer value (HRST) is found to have expired in step 394, then the redistribution for VF is also executed in step 395, thereby adding the counts within the ST, VT 1:1 and VT not 1:1 bins to the VF bin and effectively enabling therapy at step 416. The HRST timer is reset whenever normal sinus rhythm is detected within step 392 or whenever therapy is administered in step 416.

At step 398, the stimulation device determines whether at least $X_3$ of the last Y events in the circular buffer are set to VT not 1:1 and, if so, step 400 is performed wherein the bins are redistributed to add each of the counts within the ST and VT 1:1 bins to the VT not 1:1 bin. The ST, VT 1:1 and AF bins are then all cleared. The redistribution is performed to account for the possibility that some VT not 1:1 events were erroneously given a preliminary classification of either ST, VT 1:1.

At step 402, the stimulation device determines whether at least $X_4$ of the last Y events in the circular buffer are set to VT 1:1 and, if so, step 404 is performed wherein the bins are redistributed to add each of the counts within the ST, VT not 1:1 and VF bins to the VT 1:1 bin. The ST, VT not 1:1, VF and AF bins are then all cleared. The redistribution is performed to account for the possibility that some VT 1:1 events were erroneously given a preliminary classification of either ST, VT not 1:1, VF or AF.

At step 406, the stimulation device determines whether at least $X_5$ of the last Y events in the circular buffer are set to ST and, if so, step 408 is performed wherein the bins are redistributed to add each of the counts within the VT not 1:1 and VF bins to the VT 1:1 bin. This is done in case ST was incorrectly diagnosed and the bins were full of VT 1:1, VT not 1:1, or VF. In that case, ST diagnosis is overridden and VT 1:1 is diagnosed. The AF, VT, and VF bins are then all cleared.

At step 410, the stimulation device determines whether at least $X_6$ of the last Y events in the circular buffer are set to AF and, if so, step 412 is performed wherein the ST, VT 1:1, and VT not 1:1 bins are all cleared. No counters are added to any of the other bins. The ST, VT 1:1 and the VT not 1:1 bins are cleared since it is likely that the counts therein were the result of an erroneous preliminary classification.

Execution proceeds to step 414, wherein the stimulation device determines whether the counts within any of the running total bins exceeds a corresponding running total threshold value and, if so, a final decision as to the current arrhythmia, if any, of the heart is thereby triggered and appropriate therapy is administered at step 416. (Here it should be noted that one of the running total bins may be found to have exceeded its respective threshold at step 414 even though no redistribution took place immediately prior thereto because the threshold may have been reached merely as a result of the incrementing of the bins occurring within one of step 316 (FIG. 7) or steps 358, 362, 366, 370, 372, 377 or 380 (FIG. 10).) If therapy had been administered, then all the bins are cleared, the HRST is reset, and execution returns to the "start" in FIG. 7 to continue to monitor the heart to determine whether any subsequent therapy is necessary.

Figure 7:
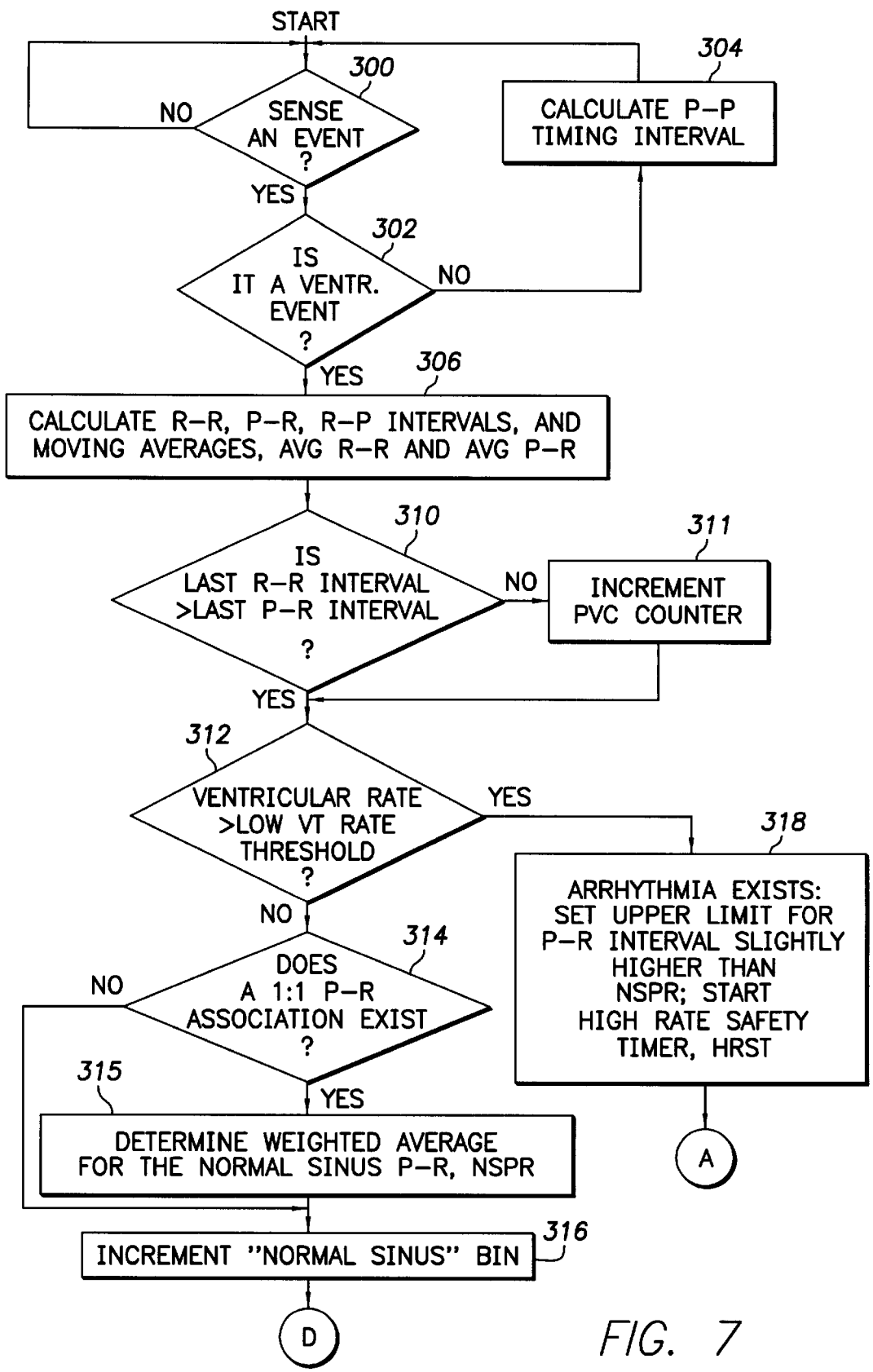
FIGS. 7–12 together provide a detailed flow chart illustrating a particular method corresponding to the general method of FIG. 2.

If none of the running total bins exceeds its corresponding threshold, then the analysis of the current state of the heart is inconclusive, step 418, and execution also returns to the "start" in FIG. 7, wherein another event is sensed and analyzed.

Thus, FIGS. 7–12 illustrate in detail a technique for use in a stimulation device for discriminating among various type of arrhythmias based, in part, upon whether running total thresholds have been exceeded wherein the running total thresholds are selectively redistributed to account for common event classification errors. Alternative stimulation devices may incorporate only some of the many features set forth in FIGS. 7–11. Also, other implantable stimulation devices, such as pacemakers, may incorporate some of the features as well. Additionally, features not specifically shown in FIGS. 7–11 (e.g., a bin for high rate VT, SVT 1:1, etc.) may also be incorporated. One additional feature not shown in FIGS. 7–11 is the incorporation of a heart rate boundary zone for use in classifying events as VT or VF. Consider an implementation wherein the VT lower zone cutoff is 120 bpm and the VT upper zone cutoff is 180 bpm. Any events detected at a heart rate below 180 may be classified as, for example, VT not 1:1, or VT 1:1. Any events detected at a heart rate above 180 bpm may be classified as a VF. If the arrhythmia is about 180 bpm, the rate may sometimes be measured as 179 and sometimes as 181 because of quantization errors and other instabilities. So some events may be classified as a VT and others as a VF resulting in a possible delay in administering therapy. To avoid this possible problem, a boundary, or hysteresis zone, is set between 175–185 bpm. If the heart rate falls within this zone, the VF bin and one of the VT bins (either VT not 1:1 or VT 1:1) are incremented and the event counts against the X out of the last Y events in the circular buffer sliding total criteria for both VT and VF.

What has been described are systems for discriminating among various atrial and ventricular arrhythmias using an implantable stimulation device. The various functional components of the exemplary device may be implemented using any appropriate technology including, for example, microprocessors running software programs or application specific integrated circuits (ASIC'S) executing combinatorial logic operations. Although described primarily with respect to a stimulation device, aspects of the invention are applicable to other implantable stimulation devices, such as pacemakers. The exemplary embodiments of the invention described herein are merely illustrative of the invention and should not be construed as limiting the scope of the invention.

What is claimed is:

1. In an implantable stimulation device, a method for discriminating various arrhythmias of a patient's heart, the method comprising the steps of:

detecting cardiac events within the heart beginning at an initial point in time;

determining a preliminary classification for each cardiac event for a plurality of heart rhythms to establish predetermined classifications;

maintaining running totals of the number of cardiac events within each of the predetermined classifications since the initial point in time;

maintaining sliding totals of the number of cardiac events within each of the predetermined classifications out of a group of most recent cardiac events;

determining whether the sliding total in any one of the predetermined classifications exceeds a corresponding predetermined sliding total threshold and, if so, selectively redistributing the running totals of the predetermined classifications since the initial point in time; and determining whether the redistributed running total in any one of the predetermined classifications exceeds a corresponding predetermined running total threshold and, if so, identifying the patient's heart rhythm as being the heart rhythm corresponding to the predetermined classification in which the predetermined running total threshold was exceeded.

2. The method of claim 1, wherein the preliminary classifications for the plurality of heart rhythms include normal sinus rhythm (NSR), ventricular fibrillation (VF), ventricular tachycardia without 1:1 retrograde conduction (VT not 1:1), ventricular tachycardia with 1:1 retrograde conduction (VT 1:1), atrial fibrillation (AF) and sinus tachycardia (ST).

3. The method of claim 2, wherein the step of selectively redistributing the running totals comprises the step of:

clearing the running totals of all of the predetermined classifications whenever the sliding total for the preliminary classification of normal sinus rhythm (NSR) exceeds the corresponding predetermined sliding total threshold.

4. The method of claim 2, wherein the step of selectively redistributing the running totals comprises the steps of:

adding the running totals for ST, VT 1:1 and VT not 1:1 to the running total for VF and then clearing the running totals for ST, VT 1:1, VT not 1:1 and AF, whenever the sliding total having a preliminary classification of VF exceeds the corresponding predetermined sliding total threshold.

5. The method of claim 4, the step of selectively redistributing the running totals comprises the steps of:

tracking the amount of time elapsed following an R-R interval which has a corresponding ventricular rate that exceeds a predetermined rate threshold indicative of a tachyarrhythmia; and adding the running totals for ST, VT 1:1 and VT not 1:1 to the running total for VF, and then clearing the running totals for ST, VT 1:1, VT not 1:1 and AF, whenever the amount of elapsed time exceeds a predetermined threshold.

6. The method of claim 2, wherein the step of selectively redistributing the running totals comprises the steps of:

adding the running totals for ST and VT 1:1 to the running total for VT not 1:1, and then clearing the running totals for ST, VT 1:1, and AF, whenever the sliding total having a preliminary classification of VT not 1:1 exceeds the corresponding predetermined sliding total threshold.

7. The method of claim 2, wherein the step of selectively redistributing the running totals comprises the steps of:

adding the running totals for ST, VT not 1:1 and VF to the running total for VT 1:1, and then clearing the running totals for ST, VT not 1:1, VF and AF, whenever the sliding total having a preliminary classification of VT 1:1 exceeds the corresponding predetermined sliding total threshold.

8. The method of claim 2, wherein the step of selectively redistributing the running totals comprises the steps of:

adding the running totals for VT not 1:1 and VF to the running total for VT 1:1, and then clearing the running totals for VT not 1:1, VF and AF, whenever the sliding total having a preliminary classification of ST exceeds the corresponding predetermined sliding total threshold.

9. The method of claim 2, wherein the step of selectively redistributing the running totals comprises the step of:

clearing the running totals for ST, VT 1:1, and VT not 1:1, whenever the sliding total having a preliminary classification of AF exceeds the corresponding predetermined sliding total threshold.

10. The method of claim 1, wherein the step of determining a preliminary classification for each detected cardiac event comprises the steps of:

determining that the heart rate is greater than a low tachycardia rate zone; and assigning a preliminary classification of VF when the cardiac event is greater than the tachycardia rate zone.

11. The method of claim 1, wherein the step of determining a preliminary classification for each detected cardiac event comprises the steps of:
determining that the heart rate is within a low tachycardia rate zone; and determining that a 1:1 P-R association does exist.

12. The method of claim 11, wherein the step of determining a preliminary classification for each detected cardiac event further comprises the steps of:
determining whether the cardiac event is a premature ventricular complex (PVC); and
assigning a preliminary classification of VT not 1:1 when the cardiac event is determined to be a PVC.

13. The method of claim 11, wherein the step of determining a preliminary classification for each detected cardiac event further comprises the steps of:
determining if the P-R interval is between predetermined maximum and minimum thresholds; and
assigning a preliminary classification of VT 1:1 when the P-R interval is not between the predetermined maximum and minimum thresholds.

14. The method of claim 11, wherein the means for determining a preliminary classification for each detected cardiac event further comprises the steps of:
determining whether the P-R intervals are stable;
assigning a preliminary classification of VT 1:1 when the P-R interval is not stable and is between the predetermined maximum and minimum thresholds; and
assigning a preliminary classification of ST when the P-R interval is stable and is between the predetermined maximum and minimum thresholds.

15. The method of claim 1, wherein the step of determining a preliminary classification for each cardiac event further comprises the steps of:
determining that the heart rate is within a tachycardia rate zone; and determining that a 1:1 P-R association does not exist.

16. The method of claim 15, wherein the step of determining a preliminary classification for each cardiac event further comprises the steps of:
determining that the atrial rate does not exceed the ventricular rate; and
assigning a preliminary classification of VT not 1:1.

17. The method of claim 15, wherein the step of determining a preliminary classification for each cardiac event further comprises the steps of:
determining that the atrial rate does exceed the ventricular rate;
determining if the R-R interval is stable; and
assigning a preliminary classification of AF when the R-R is not stable.

18. The method of claim 17, wherein the step of determining a preliminary classification for each cardiac event further comprises the steps of:
determining whether the R-P intervals are stable;
assigning a preliminary classification of AF when the R-R intervals are stable and the R-P interval is stable; and
assigning a preliminary classification of VT not 1:1 when the R-R intervals are stable and the R-P interval is not stable.

19. An implantable stimulation device having means for discriminating various arrhythmias of a patient's heart and for applying therapy in response thereto, comprising:

a sensing circuit that senses cardiac events;
a memory coupled to the sensing circuit to store a sequence of cardiac events, the memory including a circular buffer for storing a predetermined number of cardiac events that occurred most recently within the sequence;
a control circuit coupled to the sensing circuit to determine a preliminary classification for each sensed cardiac event to establish predetermined classifications;
a first counter coupled to the memory to count a running total for each of the cardiac events within each of the predetermined classifications based on all cardiac events sensed from an initial point in time;
a second counter coupled to the memory to count a sliding total for each of the cardiac events within each of the predetermined classifications based on the cardiac events contained within the circular buffer;
the control circuit further comprising:
a first detector that detects when the sliding total of any one of the predetermined classifications exceeds a corresponding sliding total threshold;
means, coupled to the first detector, for redistributing the running totals of the predetermined classifications since the initial point in time whenever one of the sliding total exceeds its corresponding sliding total threshold;
a second detector that detects when the redistributed running total of any one of the predetermined classifications exceeds a corresponding running total threshold; and
means, coupled to the second detector, for identifying the patient's heart rhythm as being the rhythm corresponding to the predetermined classification which exceeds a corresponding running total threshold.

20. The device of claim 19, wherein the predetermined classifications includes at least normal sinus rhythm (NSR), ventricular fibrillation (VF), ventricular tachycardia without 1:1 retrograde conduction (VT not 1:1), ventricular tachycardia with 1:1 retrograde conduction (VT 1:1), atrial fibrillation (AF), and sinus tachycardia (ST).

21. The device of claim 20, wherein the control circuit further comprises:
timing means for determining a plurality of timing characteristics of atrial and ventricular rhythms, including determining a ventricular rate corresponding to an R-R interval, an atrial rate corresponding to a P-P interval, an R-P interval, and a P-R interval;
means, coupled to the timing means, for determining if a 1:1 P-R association exists, and
means for determining the preliminary classification of VF, VT not 1:1, or VT 1:1 based on the ventricular rate and the presence of absence of a 1:1 P-R association.

22. The device of claim 21, wherein:
the timing means further includes means for determining a presence of a premature ventricular complex (PVC), an indicator that the R-R interval is stable, an indicator that the R-P interval is stable, an indicator that a P-R interval is physiologic, an Indicator that a P-R interval is stable, and an indicator when the ventricular rate is either above, or within, a high rate zone; and
means, coupled to the timing means, for determining a preliminary classification of VT not 1:1, VT 1:1, ST, or AF based on the plurality of ventricular and atrial timing characteristics.

23. The device of claim 22, wherein the control circuit determines a preliminary classification of VT not 1:1 whenever one of the following is detected:

a 1:1 P-R association exists but was due to a PVC;

a 1:1 P-R association does not exist and the ventricular rate exceeds the atrial rate; and a 1:1 P-R association does not exist and the atrial rate exceeds the ventricular rate together with a stable R-R interval and an unstable R-P interval.

24. The device of claim 22, wherein the control circuit determines a preliminary classification of ST whenever the following is detected:

a 1:1 P-R association does exists together with a physiological P-R interval and a stable P-R interval.

25. The device of claim 24, further comprising:

means for detecting a physiological need for a high atrial heart rate;

means for identifying the event as a pathological SVT 1:1 when a physiological need does not exist; and identifying the event as a physiological ST when physiological need does exist.

26. The device of claim 25, wherein the means for detecting a physiological need for a high atrial heart rate comprises:

a physiologic sensor that detects when the patient is in an exercise state thereby indicating a physiological need for a high heart rate.

27. The device of claim 25, wherein the means for detecting a physiological need for a high atrial heart rate comprises:

means for detecting slow and sudden onset of the heart rhythm, wherein a high heart rate is needed only when a slow onset occurs.

28. The device of claim 22, wherein the control circuit determines a preliminary classification of AF whenever the detection of a 1:1 P-R association does not occur, the atrial rate is detected to exceed the ventricular rate, and one of a non-stable R-R interval is detected or a stable R-R interval is detected concurrent with a stable R-P interval.

29. The device of claim 22, wherein the control circuit determines a preliminary classification of VT 1:1 whenever one of a 1:1 P-R association exists and the P-R interval is not physiologic, or a 1:1 P-R association exists, the P-R interval is physiologic, and the P-R interval is not stable.

* * * * *